(12) United States Patent
Vinogradov et al.

(10) Patent No.: US 9,500,626 B2
(45) Date of Patent: Nov. 22, 2016

(54) METHODS AND DEVICES FOR LONG TERM STRUCTURAL HEALTH MONITORING OF PIPELINES AND VESSELS

(71) Applicant: Southwest Research Institute, San Antonio, TX (US)

(72) Inventors: Sergey A. Vinogradov, San Antonio, TX (US); Matthew L. Capps, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 297 days.

(21) Appl. No.: 14/078,919

(22) Filed: Nov. 13, 2013

(65) Prior Publication Data

US 2015/0128710 A1   May 14, 2015

(51) Int. Cl.
*G01N 29/22* (2006.01)
*G01N 29/11* (2006.01)
*G01N 29/24* (2006.01)
*G01N 17/00* (2006.01)

(52) U.S. Cl.
CPC ............ *G01N 29/223* (2013.01); *G01N 17/00* (2013.01); *G01N 29/11* (2013.01); *G01N 29/2437* (2013.01); *G01N 2291/0258* (2013.01); *G01N 2291/044* (2013.01); *G01N 2291/0425* (2013.01); *G01N 2291/26* (2013.01)

(58) Field of Classification Search
CPC ...... G10K 11/004; G10K 1/10; G01N 29/22; G01N 29/223
USPC ........................ 73/866.5, 592, 627
See application file for complete search history.

(56) References Cited

U.S. PATENT DOCUMENTS

| | | | |
|---|---|---|---|
| 4,020,531 A | 5/1977 | Ahrens et al. | |
| 4,294,118 A | 10/1981 | Shiraiwa et al. | |
| 4,510,447 A | 4/1985 | Moyer | |
| 5,016,843 A | 5/1991 | Ward | |
| 5,468,025 A | 11/1995 | Adinolfe et al. | |
| 5,541,522 A | 7/1996 | Rosen et al. | |
| 6,212,944 B1* | 4/2001 | Kwun et al. | 73/116.02 |
| 6,968,727 B2 | 11/2005 | Kwun et al. | |
| 7,573,261 B1* | 8/2009 | Vinogradov | 324/240 |
| 7,942,060 B2 | 5/2011 | Suri et al. | |
| 8,098,065 B2* | 1/2012 | Kwun et al. | 324/240 |
| 8,291,780 B2 | 10/2012 | Smith et al. | |

(Continued)

OTHER PUBLICATIONS

BAPI, Clamp-On and Spring-Loaded Straps, Oct. 11, 2007.*

(Continued)

*Primary Examiner* — Hezron E Williams
*Assistant Examiner* — Xin Zhong
(74) *Attorney, Agent, or Firm* — Grossman, Tucker et al

(57) ABSTRACT

A system and method for non-destructive monitoring a component including a guided wave sensor positioned around a surface of the component, wherein the component has a perimeter. A first spring mounting clamp positioned around the component perimeter and a second spring mounting clamp positioned around the component perimeter, wherein the first and second mounting clamps are positioned a distance of 0.1 inches to 5.0 inches on either side of the guided wave sensor. A plurality of elongated springs is attached at a first end to the first spring mounting clamp and attached at a second end to the second spring mounting clamp. The central portion applying a pressure of at least 10 psi to the guided wave sensor.

17 Claims, 13 Drawing Sheets

(56) References Cited

U.S. PATENT DOCUMENTS

2011/0025317 A1 2/2011 Kwun et al.
2012/0297882 A1 11/2012 Palma et al.

OTHER PUBLICATIONS

A54 "Clamp-On & Spring-Loaded Straps, Temperature Sensors"; Building Automation Products, Inc. (BAPI), Rev. Oct. 11, 2007 (2 pgs) <<http://www.bapihvac.com>> (accessed Aug. 8, 2013).

A66 "Strap Units and Remote Probe Units, Temperature Sensors"; Building Automation Products, Inc. (BAPI), Rev. Jun. 6, 2013 (2 pgs) <<http://www.bapihvac.com>> (accessed Aug. 8, 2013).
Gottschalch, et al, "Integrated European Industrial Risk Reduction System"; Acronym: IRIS; Project No. FP7-NMP-2007-LARGE-1; WP2 Demonstration Report issued Mar. 4, 2010 (50 pgs).
Vinogradov, et al, "Magnetostrictive Sensing Probes for Guided Wave Testing of High Temperature Pipes" Materials Evaluation Technical Paper, Jun. 2014, pp. 803-811.

* cited by examiner

METHODS AND DEVICES FOR LONG TERM STRUCTURAL HEALTH MONITORING OF PIPELINES AND VESSELS

FIELD OF INVENTION

The present disclosure relates to clamping methods and clamping devices for long term structural health monitoring of pipelines and vessels and, in particular, the coupling of guided wave sensors to components for monitoring using a sensor clamp.

BACKGROUND

Guided wave testing is developing as a method of non-destructive evaluation (NDE) of anomalies in structural components. Such anomalies include the development and spread of corrosion, cracks, voids, and other defects incurred due to environmental stressors such as corrosive materials, stresses associated with use including thermal or mechanical fatigue, or discrete events such as seismic events. Guided waves may be generated directly in a component or coupled to a component using an actuator to impart ultrasonic vibrations. Guided wave testing has been used to monitor pipelines, plates, aircraft structures, bridge cables, and heat exchanger tubing.

Sensors for use in guided wave monitoring may be located adjacent to component walls or surfaces. However, thermal expansion and chemical changes, such as corrosion, may reduce the coupling between the sensors and the component surfaces. For example, pipe or hose clamps used to hold sensors in place may expand in elevated temperature conditions and fail to retain their shape, reducing the effectiveness of the coupling between the sensors and component wall surfaces. Spring loaded pipe clamps using flat or wave springs and Belleville washers exhibit relatively high profiles making it difficult to deploy the sensors in crowded areas. For example, a sensor may have a thickness about 0.125 inches, and the clamp loaded with wave springs on top of the sensor may add another inch or more. However, a gap between adjacent pipes on the order of 0.25 inches is not uncommon, leaving little room to accommodate the sensors. In addition, a clamp mounted on top of a sensor is difficult to adjust on a pipe when additional heating pipes are mounded parallel to the pipe body. In this case, the clamping ring would be positioned over the heating tubes, which may have a diameter of up to two or three inches. This may cause the set up to be bulky and expensive.

Further, flat springs, wave springs, and Belleville washers are either limited to grades of steel that typically do not operate at 500° C. or are not corrosion resistant. Thermal expansion and environmental stresses may also cause delamination of adhesives used to couple sensors to walls. Furthermore, corrosion of coupling elements may reduce coupling between sensors and components. Accordingly, there remains a need to improve the coupling of sensors to component walls and devices used therefore.

SUMMARY

An aspect of the present disclosure is directed to a system for non-destructive monitoring of a component. The system includes a guided wave sensor positioned around a surface of the component, wherein the component has a perimeter. The system also includes a first spring mounting clamp positioned around the component perimeter and a second spring mounting clamp positioned around the component perimeter, wherein the first and second mounting clamps are positioned a distance of 0.1 inches to 5.0 inches from either side of the guided wave sensor. The system further includes a plurality of elongated springs, each elongated spring including a first end, a second end opposing the first end, and a central portion between the first end and the second end. Each of the elongated springs is attached at the first end to the first spring mounting clamp and attached at the second end to the second spring mounting clamp and the central portion applies a first pressure of at least 10 psi to the guided wave sensor.

Another aspect of the present disclosure is directed to a sensor assembly for non-destructive monitoring. The assembly includes a guided wave sensor. The assembly also includes an elongated spring including a first end, a second end opposing the first end, and a central portion between the first end and the second end, wherein the central portion of the elongated spring contacts the guided wave sensor and is configured to apply pressure to the guided wave sensor. The assembly further includes a first spring mounting clamp detachably affixed to the first end of the elongated spring and a second spring mounting clamp detachably affixed to the second end of the elongated spring. The first and second spring mounting clamps are positioned a distance from the guided wave sensor on either side of the guided wave sensor. In addition, the overall height of the guided wave sensor, the elongated spring, and the first and second spring mounting clamps is in the range of 0.12 inches to 1.0 inch and the overall length is in the range of 2.0 inches to 10.0 inches. Further, the elongated spring and first and second mounting clamps are capable of applying either a constant pressure or variable pressure regime including a first pressure to the guided wave sensor at a temperature in the range of 20° C. to 25° C. and applying a second pressure to the guided wave sensor at a temperature in the range of 26° C. to 500° C., wherein the second pressure is in the range of 50% to 99% within the first pressure when the sensor clamp is mounted to a component.

Yet a further aspect of the present disclosure relates to a method of deploying a guided wave sensor. The method includes positioning a guided wave sensor around a surface of a component. The method also includes positioning at least two spring mounting clamps on either side of the guided wave sensor. The method further includes affixing an elongated spring at a first end and at a second end opposing the first end onto the spring mounting clamps and applying a pressure to the guided wave sensor coupling the guided wave sensor to the component. The pressure is at least 10 psi and the overall height of the guided wave sensor, the spring mounting clamps, and the spring is in the range of 0.12 inches to 1.0 inches and the overall length is in the range of 2.0 inches to 10.0 inches in length.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein:

FIG. 1b illustrates a close-up view of a portion of FIG. 1a;

DETAILED DESCRIPTION

Figure 1B:
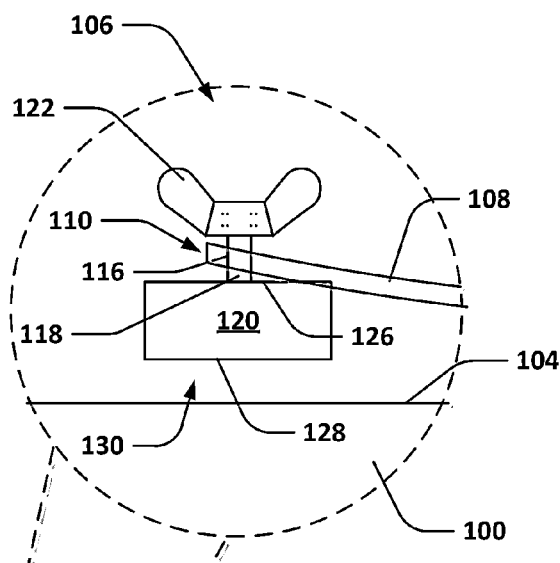
Figure 1A:
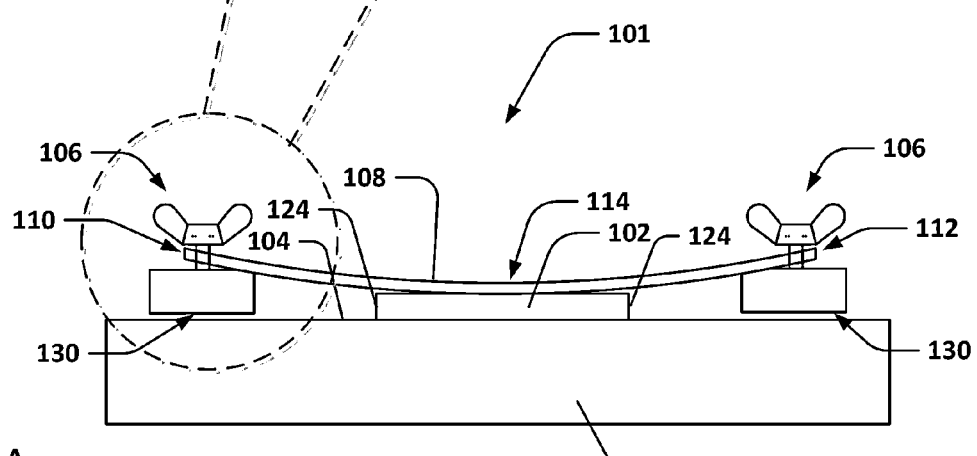
FIG. 1a illustrates a cross-sectional view of an embodiment of a sensor clamp and spring for coupling a magnetostrictive sensor to a component; the cross-section is taken through a wall of a cylindrical body as illustrated in FIG. 3.
Figure 1A:

The present disclosure is directed to devices and methods for non-destructive, long term structural health monitoring of pipelines and vessels and, in particular, the coupling of guided wave sensors to component surfaces with a sensor clamp. In particular, the sensor clamps utilize one or more springs to apply pressure to the sensor against a component surface, where the springs span the sensor and are held in place using spring mounting clamps. The arrangement described herein provides a clamping force of at least 10 psi and up to 100 psi on the sensor with an overall height of the sensor clamp and sensor in the range of 0.12 inches to 1.00 inches, including all values and ranges therein, such as 0.125 inches to 0.50 inches, providing a relatively low profile. In embodiments, the sensor clamps also provide continuous pressure at elevated temperatures of up to 500° C. Further, in embodiments, the arrangement holds the spring mounting clamps offset from the surface of the component so as not to interfere with the guided wave measurements.

Components that are suited for non-destructive testing, and particularly long term non-destructive testing, include structural components such as, but not limited to, bridge cables, anchor rods, braces, building components, aircraft structure, pipelines, plates, and heat exchanger tubes. The components are formed from one or more of the following: metals, metal alloys, and ceramic composites. In examples, the components take the form of plate, sheet, ribbon, flat bar, square bar, hex bar, tubes of varying cross-section, pipe, or cable. Thus, the components exhibit perimeters being one or more of square, hex, octagonal, rectangular and circular in shape. Guided waves are generated using an actuator that induces vibrations at sonic or ultrasonic frequencies within the component. The reflected guided waves are then detected by the actuators as well. The guided wave sensors include electromechanical devices, such as for example, piezoelectric actuators and magnetostrictive actuators. The actuators act as guided wave transmitters, guided wave receivers, or combinations thereof.

An estimate of anomalies in the component, such as corrosion metal loss, the development of cracks or voids, and other anomalies are obtained through measurements associated with the sensors. Guided waves are understood as mechanical or elastic stress waves in ultrasonic or sonic frequencies, 1 kHz to 1500 kHz, including all values and ranges therein, and preferably in the range of 10 kHz to 250 kHz and more preferably in the range of 20 kHz to 150 kHz. The waves propagate through in the bounded component and are considered guided as they travel through the component guided by the geometric boundaries of the component. Guided wave sensors employ one or more modes of propagating the waves including longitudinal, torsional or flexural waves. Attenuation of reflected waves detected by the sensor serves as an indicator of corrosion.

Referring now to the sensors described above, piezo actuators are understood to convert electrical signals into a controlled physical displacement and convert physical displacement into signals. A single transducer may be used to generate guided waves in the component and receive reflected guided waves or multiple transducers may be used, wherein one or more transducers generate the guided waves in a component and one or more separate transducers receive reflected guided waves. Piezo actuators may be coupled at a "pin point" location, which encompasses less than the entire circumference of a pipe, and require relatively low pressure in the range of 10 to 30 psi, including all values and ranges therein, and preferably 20 psi, to transmit energy. When piezo actuators are placed around just a portion of a pipe circumference, for example, these actuators, in comparison to the magnetostrictive actuators discussed below, provide relatively low signal quality. Furthermore, piezo actuators may exhibit a relatively high profile, such as in the range of 0.4 inches to 0.8 inches, as compared to the magnetostrictive actuators.

Magnetostrictive actuators are understood to rely upon the magnetostrictive or joule effect, wherein the manifestation of small changes in the physical dimensions of a ferromagnetic material caused by an externally applied magnetic field induces vibrations in the component. Further, the magnetostrictive actuators are understood to rely upon the inverse magnetostrictive or Villari effect, wherein vibrations (reflected) cause mechanical stress or strain that induces an electric signal by a change of magnetic induction. Magnetostrictive actuators may cover the entire circumference of a pipe, for example, thereby providing improved signal resolution over pinpoint sensors, such as the piezo actuators described above. In addition, magnetostrictive actuators may generally have a lower profile of 0.03 inches to 0.13 inches, which is less than piezo actuators, allowing magnetostrictive actuators to be used for applications where there is little clearance around the component to be measured. On the other hand magnetostrictive actuators generally require the application of relatively more pressure to provide the same rate of pressure when compared to piezoelectric actuators.

The pressure applied to sensors and particularly to a magnetostrictive actuator is preferably distributed relatively evenly across the entire contact area between the actuators and the component surface and variation in pressure applied across a surface of the actuator should be less than +/−20%. This can be challenging to accomplish, particularly at elevated or cycling temperatures due to thermal expansion and creep. Accordingly, the present disclosure is directed to providing a sensor and sensor clamp that maintains relatively even pressure across an actuator across the surface of the actuator through high temperature and cycling temperature conditions.

Figure 2:
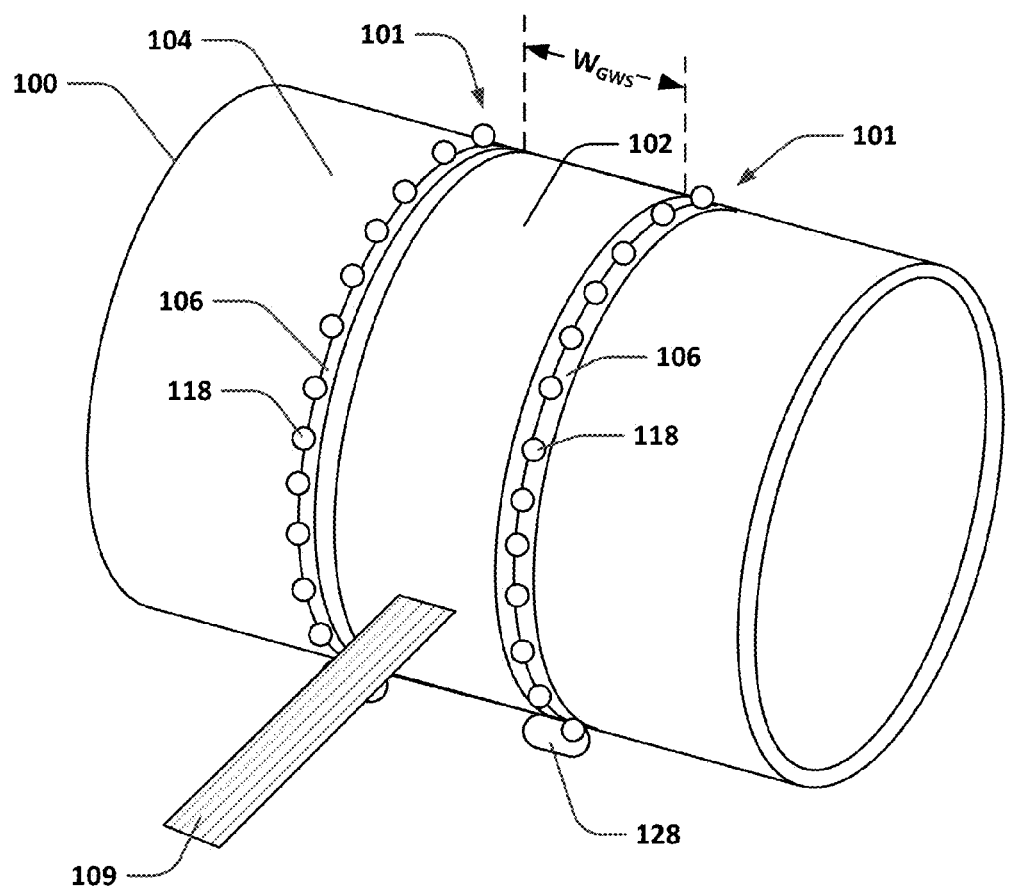
FIG. 2 illustrates a perspective view of the embodiment of FIG. 1 illustrating a magnetostrictive sensor positioned around the periphery of a cylindrical component, including a spring mounting clamp positioned on either side of the sensor at a distance from the sensor (the springs are not mounted on the mounting clamps in this figure)
Figure 3:
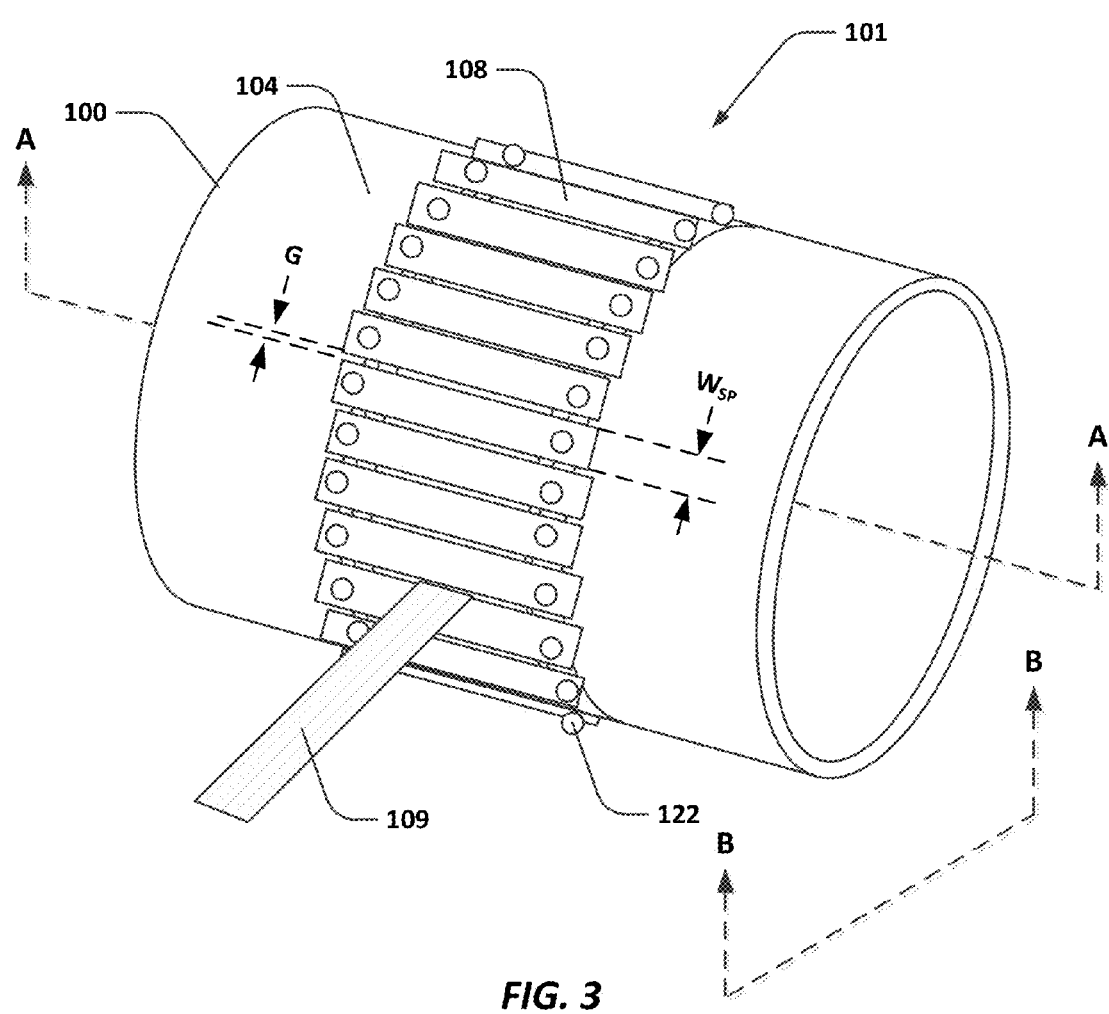
FIG. 3 illustrates a perspective view of the embodiment of FIGS. 1 and 2 illustrating the springs mounted on the mounting clamps and where the cross-sectional view of FIGS. 1 and 4 (discussed further herein) was taken.

FIGS. 1a, 1b, and 2 through 5 illustrate an embodiment of a sensor clamp 101 mounted on a component 100 for non-destructive, long term guided wave sensor testing. As illustrated, one or more sensors 102 (or actuators) are held against a component surface 104 using the sensor clamp 101 including an elongated spring 108 supported by mounting clamps 106. The sensor 102 illustrated is a magnetostrictive actuator; however, piezo actuators may also be employed in addition to or alternative to magnetostrictive actuators. In embodiments, the sensor is arranged in a flat, curvate or tubular manner. The ribbon cable 109 for actuating the sensor and sending information, such as signals, back to a controller may protrude from between adjacent springs, as illustrated in FIG. 3.

The sensor may be positioned around at least 5% of the periphery of a component and preferably around the entire periphery of the component, including all values and ranges from 5% to 100%, and preferably in the range of 50% to 100% and more preferably in the range of 80% to 100%. In the case of a pipe, for example, the sensor may be positioned around at least 5% of the pipe circumference and preferably around the entire pipe circumference, including all values and ranges from 5% to 100%, and preferably in the range of 50% to 100% around the circumference of the pipe and more preferably in the range of 80% to 100% around the circumference of the pipe. FIG. 2 illustrates an embodiment wherein a tubular shaped magnetostrictive actuator 102 is positioned around the entire circumference, or 100% of the periphery, of a pipe 100. In particular embodiments, the guided wave sensor 102 has a length $L_{GWS}$ in the range of 2.00 inches to 150.0 inches, a width $W_{GWS}$ in the range of 0.5 inches to 4 inches, and a thickness in $T_{GWS}$ the range of 0.1 inches to 0.5 inches and can accommodate component peripheries of up to 150 inches length, such as in the range of 2 inches to 150 inches in length. In embodiments, to cover the periphery of a component, one sensor or multiple sensors may be employed. In the case of multiple sensors, the sensors may be connected in parallel, which exhibits relatively lower impedance, or sequentially, which exhibits relatively higher sensitivity. Further, a parallel connection may be used on the transmitter side, while a sequential connection may be used on the receiver side.

Referring to FIGS. 1a and 1b again, the elongated spring 108 applies pressure to the sensor against the component surface 104. With respect to the elongated spring, elongated is understood to imply that the length of the spring $L_{SP}$ (see FIG. 5) is greater than the width of the spring $W_{SP}$ (see FIG. 3), wherein the spring length $L_{SP}$ is the length between the first end 110 of the spring to the second of the spring 112. The second end 112 of the spring opposing the first end 110 of the spring (see, e.g., FIG. 5). The width of the spring is understood to be perpendicular to the length. In embodiments, the spring 108 has a length $L_{SP}$ in the range of 2.00 inches to 10.00 inches, a width $W_{SP}$ in the range of 0.1 inches to 2.0 inches, and a thickness $T_{SP}$ in the range of 0.05 inches to 0.25 inches, including all values and ranges therein.

In particular embodiments, the spring 108 is a leaf spring. A leaf spring is understood to exhibit an arcuate geometry, i.e., a smooth curve extending from one end of the spring to the other. In embodiments, the leaf spring exhibits a semi-elliptic configuration; however, the leaf spring can alternatively be a three quarter-elliptic spring. In examples, the spring may include more than one spring stacked one on top of the other, wherein each spring is progressively shorter approaching the sensor, such that the shortest spring is proximal to the sensor. Alternatively, other elongate biasable members may be used as well that do not necessarily exhibit the continuous arcuate geometry of a leaf spring. For example, the spring may exhibit a generally u-shaped cross-section.

The spring 108 applies pressure to at least 20% of the surface area of the sensor 102, including all values and ranges from 20% to 100%, including all values and ranges therein, preferably in the range of 20% to 80% and more preferably in the range of 40% to 60%, etc. Or, one or more springs may be positioned across the surface of the sensor so as to provide relatively consistent pressure across the entire surface of the sensor. In embodiments, the pressure applied by the spring is in the range of 10 psi to 100 psi at room temperature (R.T., which is understood to include temperatures in the range of 20° C. to 25° C.) including all values and ranges therein and preferably from 20 to 80 psi and more preferably from 20 psi to 60 psi at R.T. and most preferably from 35 psi to 45 psi at R.T. As noted above, a pressure variation of +/−20% or less is exhibited at any point across the surface area of the sensor. FIG. 3 illustrates an arrangement of a plurality of leaf springs 108 biasing the sensor 102 (not seen) around the circumference 108 of the pipe 100.

The spring also retains its bias (or curvature) at elevated temperatures of up to 500° C., including all values and ranges from 26° C. to 500° C., 26° C. to 400° C., etc. Retaining a bias is understood to imply that the spring is capable of applying pressure to the component at elevated temperatures in the range of 50% to 99% of the pressure applied at room temperature, and preferably from 60% to 99% of the pressures applied at room temperature, and more preferably from 70% to 99% of the pressure applied at room temperature. Furthermore, the spring exhibits thermal recovery, which is understood to imply that after thermal cycling, the spring exhibits dimensions that are within 10% of its original dimensions of length, width, height, and curvature depth.

The spring is formed from a corrosion resistant alloy allowing for deployment of the sensor in humid and salty conditions, such as in refineries or other process plants near shorelines. Corrosion resistance is understood as the ability to withstand deterioration and chemical breakdown that occurs during surface exposure to the surrounding environment. Factors influencing corrosion include an alloy's reactivity to oxygen as well as surrounding environmental conditions such as resistivity, temperature changes, acidity and ionic species present in the environment. In embodiments, the alloy exhibits oxidation resistance at temperatures of up to 1,250° C., including all values and ranges from 1,000° C. to 1,250° C. and preferably in the range of 1,100° C. to 1,250° C. and more preferably in the range of 1,200° C. to 1,250° C., wherein a mass loss of less than 60 mg/cm$^2$ is exhibited after 500 hours, such as in the range of 500 hours to 6,000 hours. In preferred embodiments, a mass loss of less than 10 mg/cm$^2$ is exhibited at 1,100° C. in 1,000 hours. Oxidative mass loss is evaluated in an environment including air and 5% water vapor.

In embodiments, the spring is formed of a nickel based alloy, wherein the alloy is a nickel-chromium alloy. The alloy includes at least 45.0 percent by mass of nickel and preferably in the range of 45.0 percent by mass to 72.0 percent by mass. In addition, the alloy includes 14.0 percent by mass to 24.0 percent by mass chromium. In preferred embodiments, the alloy also includes iron present in the alloy in the range of 2 percent by mass to 22.5 percent by mass, manganese present in the range of 0.3 percent by mass to 1.0 percent by mass, silicon present in the range of 0.35 percent by mass to 0.5 percent by mass, carbon present in the range of 0.08 percent by mass to 0.15 percent by mass, and sulfur present in the range of 0.01 percent by mass to 0.015 percent by mass. In particularly preferred embodiments, the alloy further includes molybdenum optionally present in the range of 2.8 percent by mass to 10.0 percent by mass, niobium optionally present in the range of 0.7 percent by mass to 5.5 percent by mass, cobalt optionally present in the range of 1.0 percent by mass to 15.0 percent by mass, aluminum optionally present in the range of 0.4 percent by mass to 1.5 percent by mass, titanium optionally present in the range of 0.3 percent by mass to 2.75 percent by mass, phosphorus optionally present at 0.015 percent by mass and boron optionally present at 0.6 percent by mass. In more preferred embodiments, the alloys consist of the above named elements.

In one particularly preferred embodiment, the alloy includes or consists of nickel present at 50.0 to 55.0% by mass, chromium present at 20.0 to 24.0% by mass, cobalt present from 0.1 to 3.0% by mass, iron present in at 17.0 to 20.0% by mass, molybdenum present at 7.0 to 11.0% by mass, as well as other optional components each present at less than 2.0% by mass and preferably in the range of 0.05% by mass to 2.0% by mass, including one or more of the following: carbon, manganese, silicon, tungsten, phosphorus, and sulfur. In another particularly preferred embodiment, the alloy includes or consists of nickel present at 70.0 to 85.0% by mass, chromium present at 14.0 to 17.0% by mass, cobalt present from 0.1 to 3.0% by mass, iron present in at 5.0 to 9.0% by mass, titanium present at 2.0 to 3.0% by mass, as well as other optional components each present at less than 2.0% by mass and preferably in the range of 0.01% by mass to 2.0% by mass, including one or more of the following: aluminum, niobium, tantalum, carbon, manganese, silicon, copper, cobalt, and sulfur. Examples of alloys for use herein include INCONEL alloys 600, 617, 625, 718, HX and X-750

The springs are pre-bent and heat treated improving shape memory over non-heat treated spring profiles. In embodiments, heat treating occurs in an oven at temperatures of 900° C. to 1,200° C., including all values and ranges therein, and preferably in the range of 1,000° C. to 1,200° C. and more preferably 1,100° C. Heat treatment time is in the range of 5 minutes to 120 minutes, including all values and ranges therein, such as 30 minutes to 100 minutes, and more preferably in the range of 30 minutes to 60 minutes. Heat treatment is followed by rapid quenching, wherein the springs are removed from the oven and cooled at a cooling rate of 1,000° C. per second to 10,000° C., including all values and ranges therein. The spring is cooled for a period of time until the spring reaches 100° C. or less, such as in the range of 10° C. to 100° C. and preferably in the range of 20° C. to 75° C. In embodiments, the cooling time period is from 1 second to 10 minutes, including all values and ranges therein.

The spring 108 is secured on either end (such as first end 110 and second end 112 opposing the first end 110) relative to the surface 104 of the component 100 using preferably two spring mounting clamps. Depending on the length and configuration of the spring, more than two mounting clamps, such as in the range of three to four mounting clamps, are used to secure a spring 108 to the component surface 104. In embodiments, the spring 108 includes mounting holes 116 at either end 110, 112 of the spring that receive mounting posts 118 extending from the body 120 of the mounting clamps 106. Again, while only two holes are illustrated, additional holes may be provided depending on the configuration of the spring.

The spring 108 is secured on the mounting clamp posts by a mechanical fastener 122 that mates with the mounting posts, such as a nut, which is illustrated as a wing nut but may be a hex nut or other threaded mechanical fastener, having threads that mate with threads provided on the mounting posts. Other mechanical fasteners may be used in addition to or alternatively to threaded fasteners, such as cotter pins that are received in holes provided in the posts or retaining clips. The pressure applied by the spring 108 on the sensor may be increased by forcing the ends of the spring down on the posts towards the mounting body 120.

Figure 4:
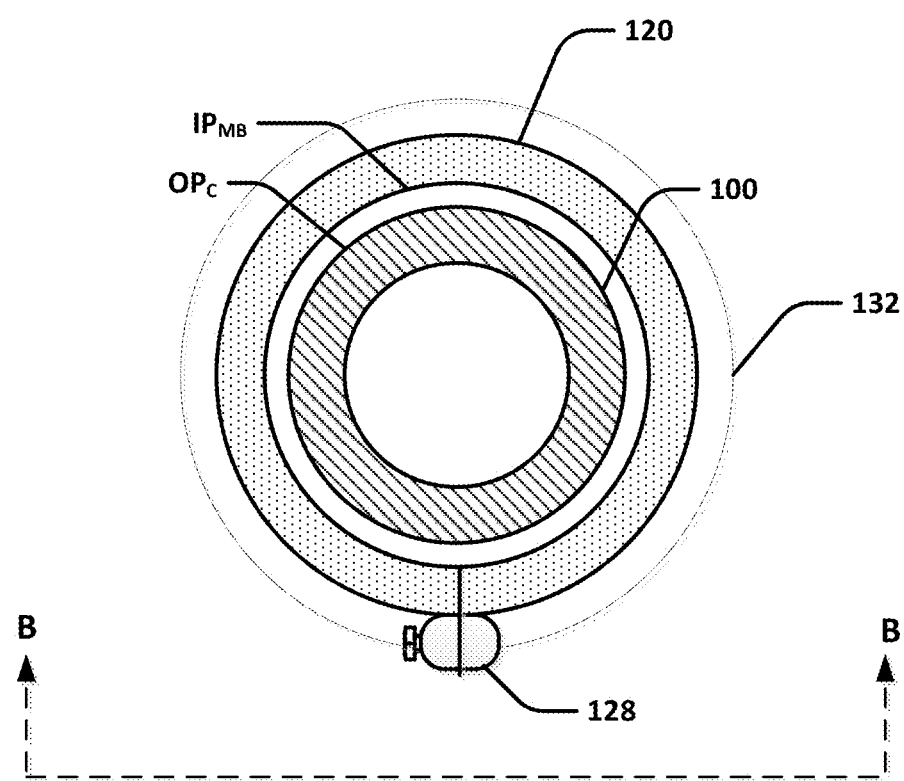
FIG. 4 illustrates a cross-sectional view of an embodiment of a component and sensor mounting clamp positioned around the periphery of a component.

As alluded to above, the spring mounting clamps 106 include a mounting body 120. The mounting body 120 in conjunction with a mounting fastener 122 affixes the spring 108 relative to the component surface 104. In embodiments, the mounting body 120 includes a strip or ribbon that is formed into a shape similar to that of the perimeter of the component to be measured and positioned around the component. As illustrated in FIG. 4, the mounting body 120 inner perimeter $IP_{MB}$ is slightly larger than the outer perimeter $OP_C$ of the component 100. In embodiments, the inner perimeter of the mounting body is equal to the perimeter of the component, such as determined by the diameter of a pipe, plus a few millimeters, such as in the range of 1 mm to 10 mm to form a gap. Thus, the inner perimeter of the mounting body is larger than the outer perimeter of the component 100. A mechanical fastener 128 is used to hold the strip together, such as a screw assembly projecting from the strip or a worm gear that interacts with features in the strip to tighten or provide slack in the size of the strip. Non-threaded fasteners may alternatively be used in embodiments. The mounting body 120 is formed from a metal or metal alloy, such as steel or stainless steel. In other embodiments the mounting body is formed of a nylon material and is in the form of a cable tie. In preferred embodiments, where the component 100 exhibits a cylindrical geometry, such as a pipe or tube, the mounting body assumes the form of a band clamp. The mounting clamp 106, including the mounting bodies 120, is located at a distance D in the range of 0.1 inches to 5.0 inches from each side 124 of the sensor 102. See FIG. 5 which illustrates that the distance D is measured from the side 124 of the sensor to the side of the mounting body 120 closest to the sensor.

In the case where a sensor is provided around less than the entire perimeter of the component, the mounting clamps are affixed to the component such as by welding, mechanical fasteners, or adhesives. In this case, there would be no gap 120 present between the mounting bodies 120 and the component surface 104.

As previously discussed above, projecting from a surface 126 of the mounting bodies 120 are one or more mounting posts 118 (depending on the number of springs to be mounted). The mounting posts exhibit a geometry selected from cylinders, squares, rectangles, or other geometric configurations. In particular embodiments, the geometry of the posts 118 match the geometry of the mounting holes 116 of the spring. Depending on the mechanism for retaining the spring 108 on the posts 118, the posts 118 may include threads or holes for securing the spring onto the posts. In embodiments, the posts 118 are formed from the same material as the mounting body 120. Alternatively, the posts 118 are formed from different materials, which are non-reactive with the material forming the mounting body in corrosive environments.

When more than one spring is provided, the mounting posts 118 are spaced along the mounting body 120 so as to space the springs apart. Spacing is generally even; however spring spacing may not be regular, particularly for irregular peripheral geometries. Preferably, when multiple springs are present, a gap G (see FIG. 3) in the range of 0.01 inches to 0.4 inches is present between the springs, including all values and ranges therein, such as 0.04 inches, 0.08 inches, etc.

The springs are arranged such that the central portion 114 of the springs are relatively lower, or closer to the component surface 104, than the ends of the springs 110, 112. This arrangement provides for the spacing of the mounting body 120 away from or off the surface 104 of the component 100, leaving a gap 130 between the bottom 128 of the mounting body 120 and the component surface 104. When the mounting body 120 is hanging in the air, suspended by the ends of the springs 110, 112, the mounting body 120 does not contact the pipe and does not interfere with measurements and avoiding unnecessary reflections produced by guided waves which would otherwise occur with mechanical contact.

Figure 5:
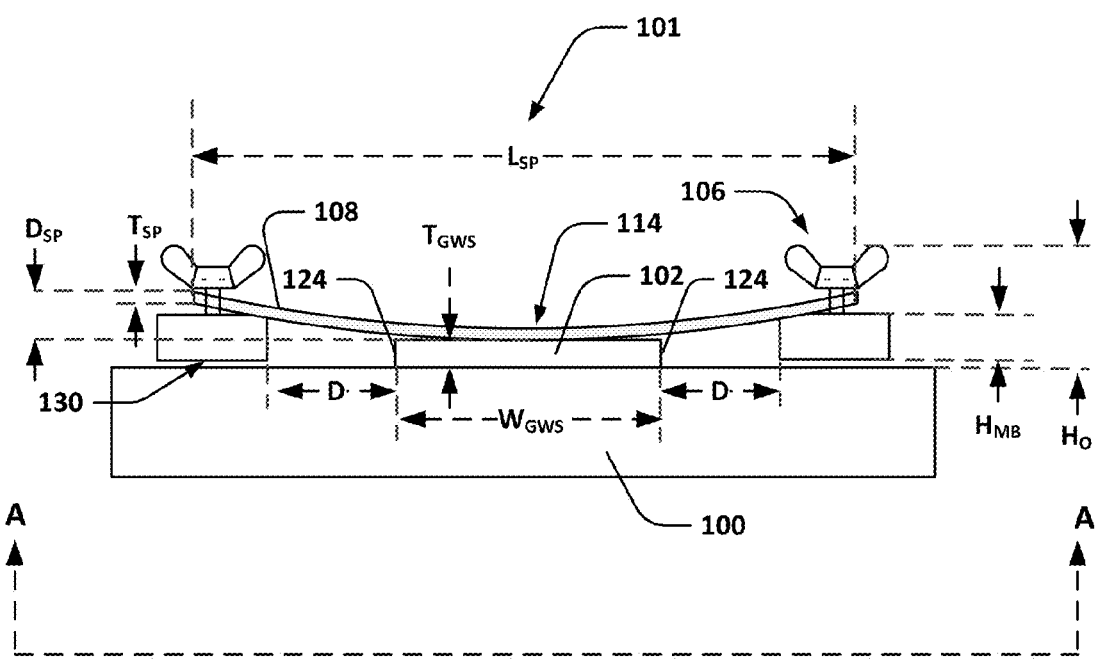
FIG. 5 illustrates the cross-sectional view of FIG. 1 including references indicating sensor thickness, spring depth, mounting body height, and overall height of the sensor clamp and sensor.

As illustrated in FIG. 5, in embodiments, the height $H_{MB}$ of the mounting body 120 is less or equal to the sensor 102 thickness $T_{GWS}$. The overall height $H_O$ of the sensor 102 and the mounting clamp 106, (including the springs, mounting body and mounting nuts), is 1.0 inch or less, such as in the range of 0.12 inches to 1.0 inches, and preferably in the range of 0.125 inches to 0.5 inches, and more preferably in the range of 0.125 inches to 0.25 inches. The ratio of the spring 108 length $L_{SP}$ to the guided wave sensor 102 width $W_{GWS}$ is in the range of 1.5:1 to 4:1 including all values and ranges therein.

Figure 6:
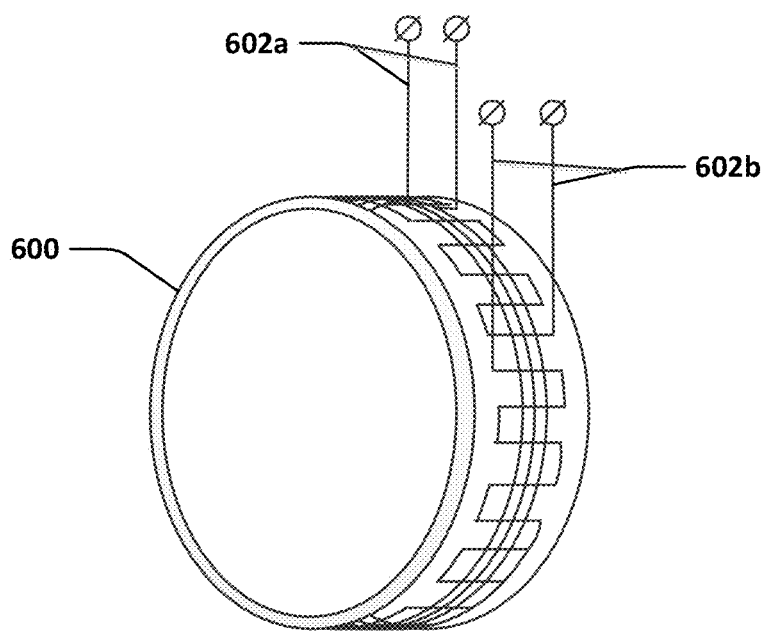
FIG. 6 illustrates an embodiment of a magnetostrictive actuator.

FIG. 6 illustrates an embodiment of a guided wave actuator for use with the sensor clamp described above. The actuator 600 includes a magnetostrictive actuator comprising an electromagnet formed of a ferromagnetic strip, which in particular embodiments may be crimped around the periphery of the strip. In embodiments, the ferromagnetic strip may be formed of an iron based ferromagnetic alloy. In embodiments, the alloy is an iron-cobalt-vanadium alloy, such as Hiperco 50 HS alloy, having the composition 48.94% iron, 48.75% cobalt, 1.90% vanadium, 0.30% niobium, 0.05% manganese, 0.05% silicon and 0.01% carbon, wherein % are atomic percent. However, other ferromagnetic alloys may be utilized as well. Wound around the actuator is one or more coils 602a, 602b to which current is applied to create a magnetic field, which may be time varying or permanent. In embodiments, one coil 602a, which wraps around the outer periphery of the strip (as illustrated around the diameter), is transverse to a second coil 602b that is looped back and forth over the surface of the strip so as to intersect the first coil around the periphery of the strip. In addition to having a profile or thickness of 0.03125 inches to 0.125 inches, in embodiments, the magnetostrictive actuator exhibits a width in the range of 1.0 inch to 5.0 inches, including all values and ranges therein.

Surrounding the actuator may be a layer of insulation 132 as illustrated in FIG. 4. The insulation may include, for example, ceramic based insulation and, preferably, the insulation includes an alumino-silicate fiber based insulation. The insulation may be provided as a blanket and wrapped around the sensor, held in place by a mechanical fastener or an adhesive. In examples, the insulation includes FIBER-FRAX blanket that available from UNIFRAX of Tonawanda, N.Y.

Figure 7:
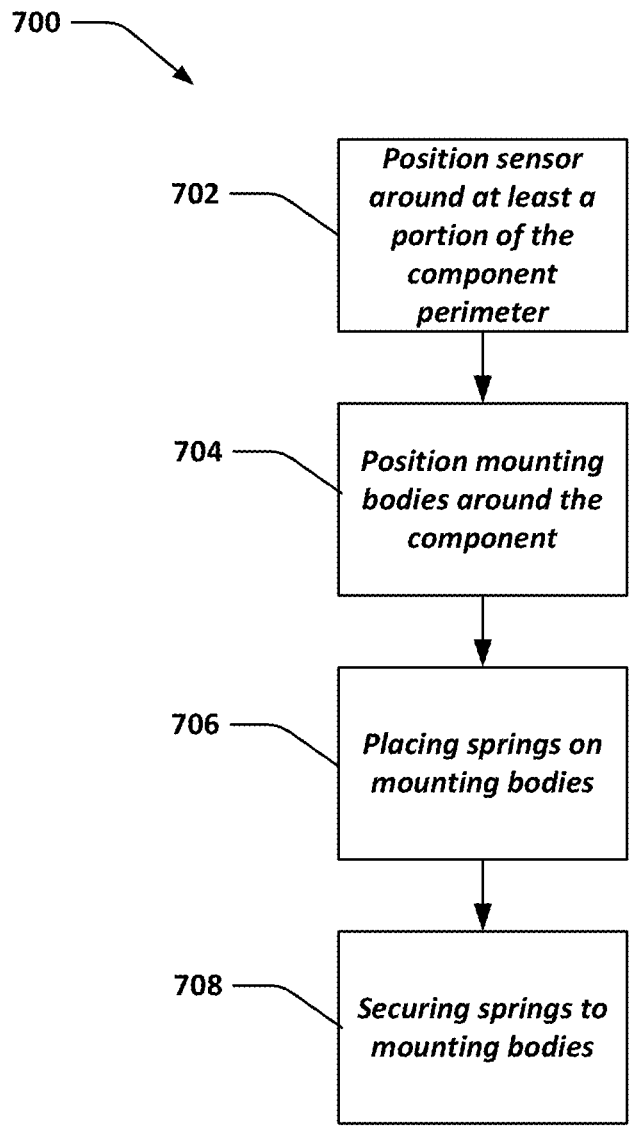
FIG. 7 illustrates a method of employing a sensor clamp for applying pressure to a sensor against a component surface.

As described above, attenuation of reflected waves detected by the sensor serves as an indication of corrosion, cracking, void formation as well as other defects that may develop in a component. FIG. 7 illustrates an embodiment of a method 700 of applying a guided wave sensor and a clamping device to a component such as a pipe. The sensor is positioned around at least a portion of the perimeter of the component and preferably around the entire component perimeter 702. The mounting clamps are positioned around the perimeter of the component as well on either side of the sensor 704. The mounting clamps are adjusted in length to provide sufficient slack to allow for a gap 130 between the component 100 and the mounting clamps 106 to form after the springs 108 are positioned on the mounting clamps 106. In embodiments, the mounting clamps 106 are placed on the component 100 after the sensor 102 is placed on the component. Alternatively, the mounting clamps 106 are placed on the component 100 before the sensor 102 is placed on the component 100. In further embodiments, a mounting clamp 106 is placed on the component 100 and then the sensor 102 is placed on the component 100 and then a second mounting clamp 106 is placed on the component 100. This may be repeated until multiple sensors and mounting clamps are placed on the component. The springs 108 are then placed on the mounting clamps 706 and the mounting nuts are tightened down on the springs 708 until a desired pressure applied to the sensor is achieved. This in turn suspends the mounting clamps off the surface of the component.

Figure 8:
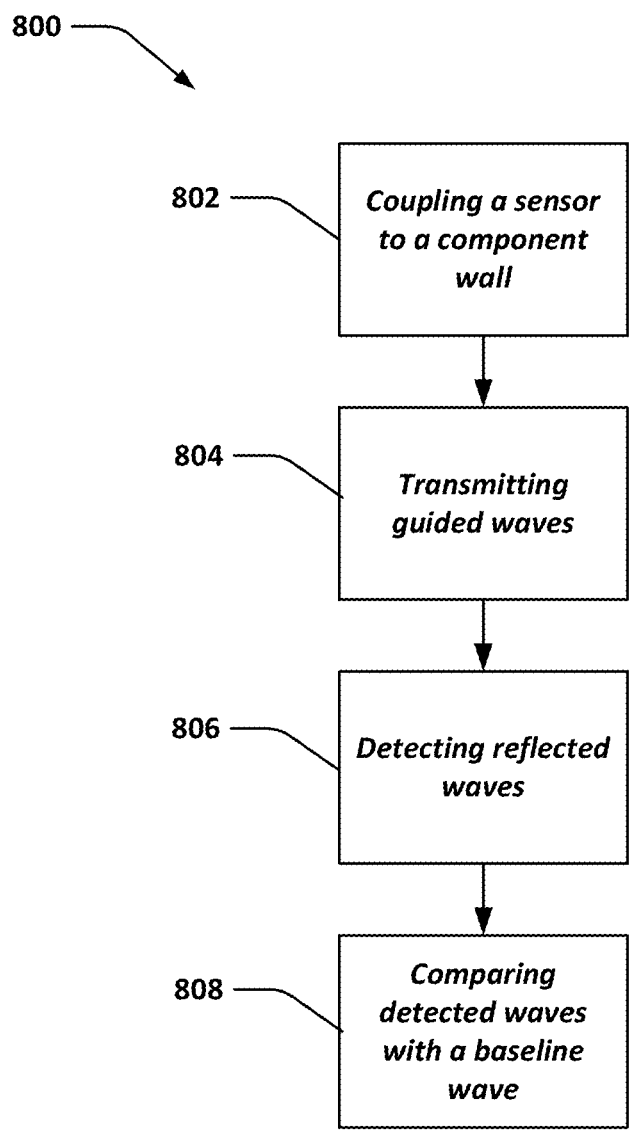
FIG. 8 illustrates a method of employing a sensor for non-destructive long term monitoring.

FIG. 8 illustrates an embodiment of a method 800 of performing non-destructive, and optionally long-term, structural health monitoring of components such as pipelines. In this embodiment, pressure is applied to a guided wave sensor against a component 802, wherein in preferred embodiments, the spring mounting clamps 806 are suspended above the guided wave sensor. The guided wave sensor, including one or more actuators, transmits one or more ultrasonic waves through the component 804 and detects reflected waves 806. The transmission of the waves is initiated by a controller, which also receives signals from the sensor that indicates the detected reflected waves. The measurement is repeated at time intervals that are either periodic or randomly selected and compared by the controller to a baseline reflected waves that are stored in memory 808. Changes in the detected reflected waves compared to the baseline reflected waves indicate anomalies that have developed, which may be caused by corrosion, cracking, void formations, other defects, or anomalies. In embodiments, the above method is performed at temperatures of up to 500° C., such as in the range of 100° C. to 500° C., preferably 250° C. to 500° C. and more preferably 400° C. to 500° C. over the course of days, weeks, months and preferably one or more years, such as in the range of two to three years.

The methods herein may be executed by the controller described above with reference to FIG. 8. The operations described herein may be implemented in a controller that includes one or more tangible storage mediums, memory, having stored thereon, individually or in combination, instructions that when executed by one or more processors perform the methods. Again, the processor may include, for example, a system CPU and/or other programmable circuitry. Also, it is intended that operations described herein may be distributed across a plurality of physical devices, such as processing structures at more than one different physical locations. The storage medium, memory, may include any type of tangible medium, for example, any type of disk including floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, magnetic or optical cards, or any type of media suitable for storing electronic instructions. Other embodiments may be implemented as software modules executed by a programmable control device.

EXAMPLES

Example 1

A guided wave sensor and sensor clamp as illustrated in FIGS. 1a, 1b and 2 through 5 was placed on a section of carbon steel pipe. The pipe had an outer diameter of 2 inches. The sensor was a magnetostrictive sensor having a geometry of ring. The leaf spring was formed from HASTELLOY and was 6.0 inches long and 0.16 inches thick. The overall height of the sensor and mounting device was 0.125 inches.

The pipe was placed in an oven and exposed to 3 heating cycles. The heating cycles began at 20° C. and the temperature was increased to 500° C. at a rate of 15° C./minute. The temperature was then reduced again to 20° C. at a rate of 5° C./minute. The overall cycle took 180 minutes. The change in force 30% produced by the springs at 500° C. is illustrated in FIG. 9 during 1 cycles.

Figure 9:
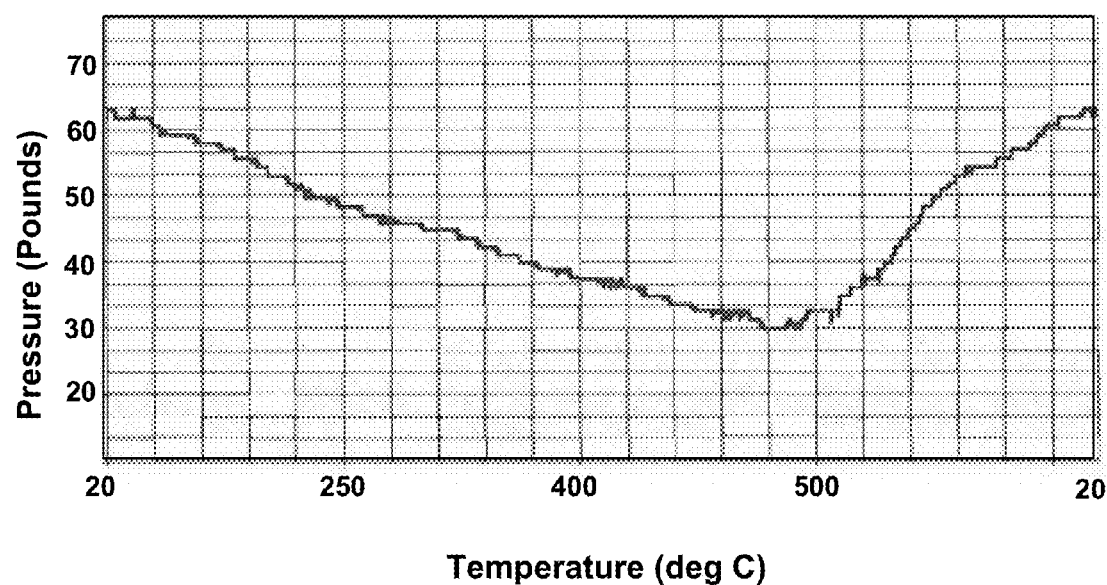
FIG. 9 illustrates a graph of temperature versus pressure, illustrating the reduction in pressure applied to the sensor against the component wall due to thermal expansion of the sensor clamp.

As seen in FIG. 9, prior to reaching the thermal peak of 500° C., the pressure applied to the dropped approximately 20 lbs from around 60 lbs at 20° C. to 40 lbs at 480° C. This was, therefore, an approximately 33% drop in pressure from the initial value. As the application of 40 lbs of pressure is considered sufficient pressure to obtain a measurement, this was considered a relatively successful result.

Example 2

Figure 10:
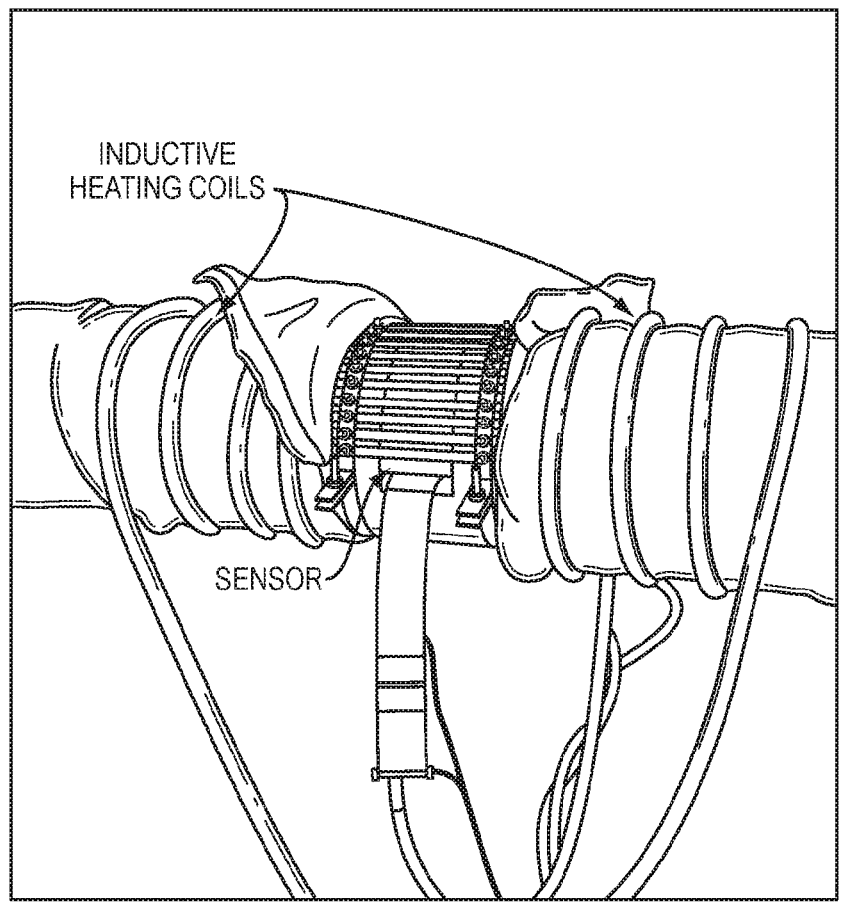
FIG. 10 illustrates a testing setup of a sensor clamp including a magnetostrictive sensor and inductive heating coils positioned around the pipe.

A guided wave sensor and sensor clamp as illustrated in FIGS. 1a, 1b and 2 through 5 was installed around a schedule 40 pipe having an outer diameter of 8 inches and 20 feet long. The pipe included a 1% cross sectional area (CSA) defect formed by drilling a 12 mm diameter×3 mm deep hole at a distance of 7 feet from the sensor. Inductive coils were wrapped around the pipe from both sides of the sensor. Five thermocouples were spot welded to the pipe for temperature control. The overall profile of the guided wave sensor, including the clamp, was 0.2 inches in height. FIG. 10 illustrates the testing setup.

Figure 11:
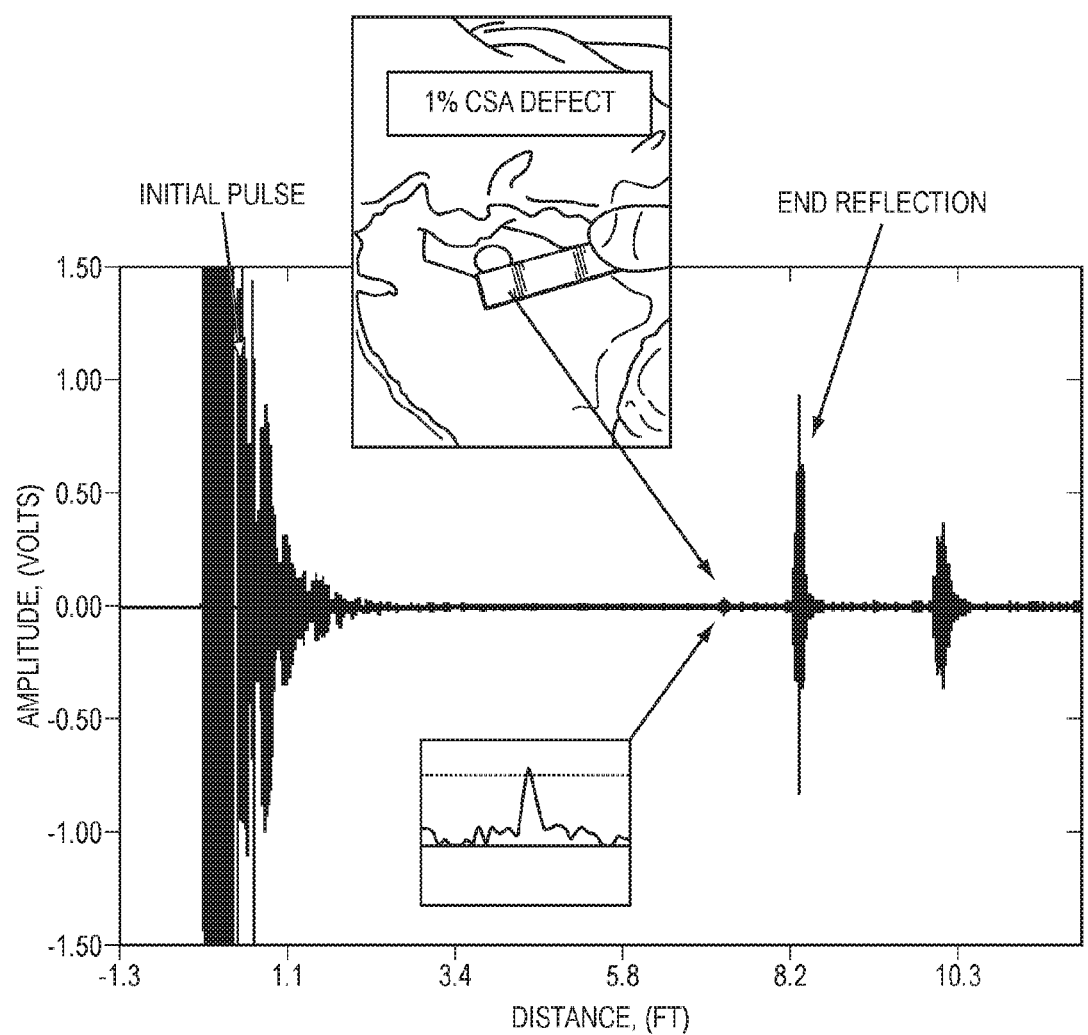
FIG. 11 illustrates a scan trace taken at 90 kHz of the pipe illustrated in the testing set up of FIG. 10.

The power output of the inductive heater was controlled such that the temperature of the pipe was adjusted to 500° C. in about 1.5 hours. A 90 kHz inspection frequency was applied to the pipe. FIG. 11 illustrates the A-scan trace obtained. The trace illustrates the initial pulse applied to the pipe, the 1% anomaly and the end reflection (i.e., the reflection generated by the end of the pipe).

Figure 12:
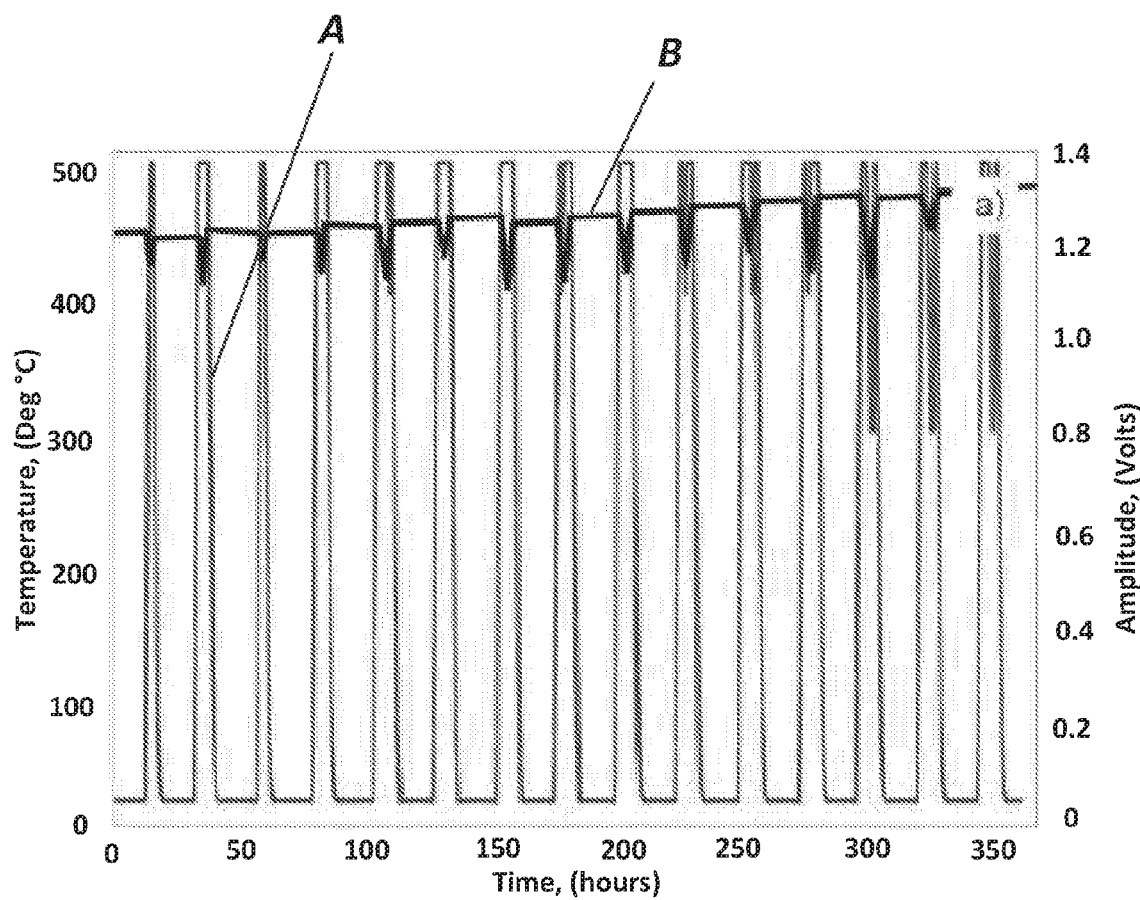
FIG. 12 illustrates a graph of temperature over time for fifteen temperature cycles as well as recorded signal amplitudes produced by the end of the pipe during temperature cycling.

Thermal cycling was performed where the pipe was cycled from 20° C. to 500° C. and back 15 times over 350 hours. The temperature progression over the 15 cycles is illustrated in FIG. 12 as line A. The recorded signal amplitude taken using a 90 kHz inspection frequency during thermal cycling produced by the end of the pipe is also illustrated as line B. A minor reduction of the signal amplitude in the middle of each temperature peak of the heating cycle was observed, illustrating the effect of heat on the measurement.

Figure 13:
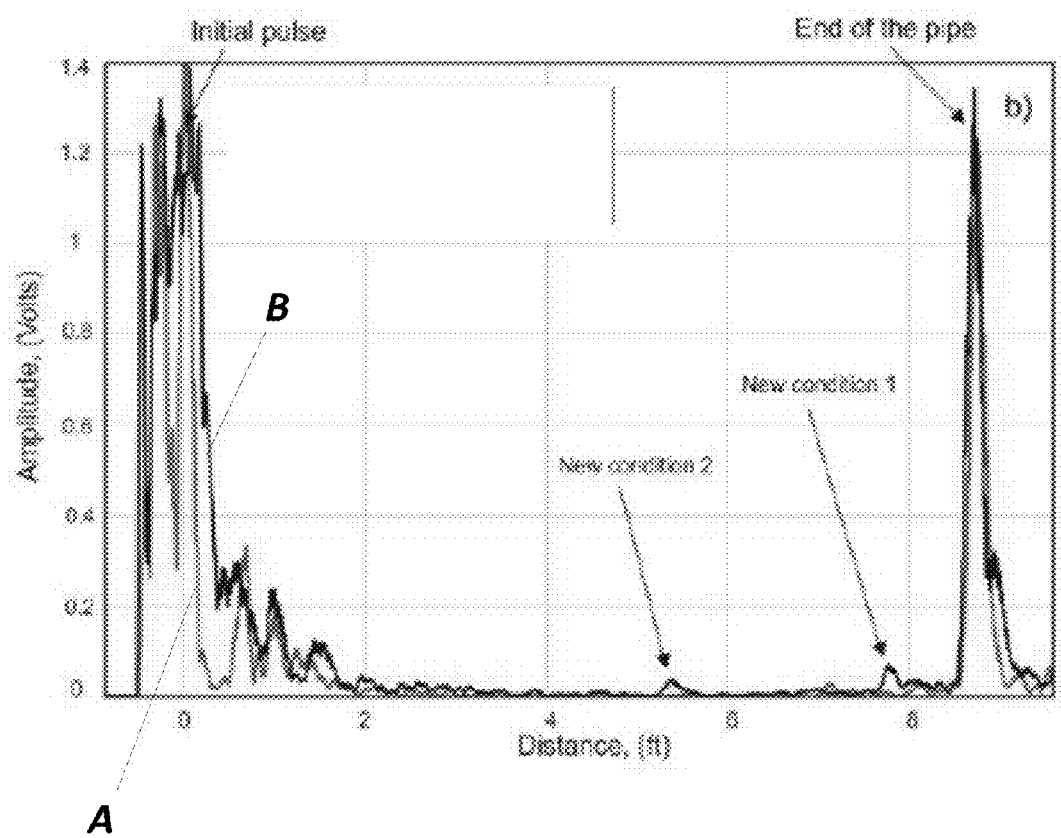
FIG. 13 illustrates scan traces taken at the beginning of cyclic temperature testing and at the end of cyclic temperature testing.

FIG. 13 illustrates an example of an A-scan trace obtained from the pipe at 90 kHz in the beginning of the testing cycle represented by line A and at the end of the testing cycle represented by line B. As can be seen, during testing two new conditions representing about a 3% cross sectional area anomaly was introduced into the pipe during the test (labeled new condition 1 and new condition 2). These indications can be clearly observed in the black trace.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A system for non-destructive monitoring of a component, comprising:
   a guided wave sensor positioned around a surface of said component, wherein said component has a perimeter;
   a first spring mounting clamp positioned around said component perimeter and a second spring mounting clamp positioned around said component perimeter, wherein said first and second mounting clamps are positioned a distance of 0.1 inches to 5.0 inches on either side of said guided wave sensor;
   a plurality of elongated springs, each elongated spring including a first end, a second end opposing said first end, and a central portion between said first end and said second end, wherein each of said elongated springs is attached at said first end to said first spring mounting clamp and attached at said second end to said second spring mounting clamp and said central portion applies a first pressure of at least 10 psi to said guided wave sensor against said component surface and;
   wherein said spring mounting clamps do not contact said component.

2. The system of claim 1, wherein said first and second spring mounting clamps each include a mounting body; and a plurality of posts extending from said mounting body on which one of said first and second ends of said plurality of elongated springs are fastened; and a plurality of removable mechanical fasteners that each mate with one of said mounting posts.

3. The system of claim 2, wherein said plurality of elongated springs each include a first mounting hole at said first end and a second mounting hole at said second end and said first and second mounting holes are positioned on said mounting posts on said first and second spring mounting clamps.

4. The system of claim 1, wherein said elongated spring and first and second mounting clamps are capable of applying said first pressure to said guided wave sensor at a temperature in the range of 20° C. to 25° C. and applying a second pressure to said guided wave sensor at an elevated temperature in the range of 26° C. to 500° C., wherein said second pressure is in the range of 50% to 99% of said first pressure.

5. The system of claim 1, wherein said perimeter assumes one or more of the following geometries: circular, square, hexagonal, rectangular, and octagonal.

6. The system of claim 1, wherein an overall height of said guided wave sensor, said elongated spring, and said spring mounting clamps is in the range of 0.12 inches to 1.0 inches.

7. The system of claim 1, wherein said elongated spring is formed from a nickel-chromium alloy heat treated at a temperature in the range of 900° C. to 1200° C. for a period of 5 to 120 minutes and retains its bias at temperatures in the range of 20° C. to 500° C.

8. A sensor assembly for non-destructive monitoring, comprising:
- a guided wave sensor;
- an elongated spring including a first end opposing a second end and a central portion between said first end and said second end, wherein said central portion of said elongated spring contacts said guided wave sensor and is configured to apply pressure to said guided wave sensor against a surface of a component;
- a first spring mounting clamp detachably affixed to said first end of said elongated spring; and
- a second spring mounting clamp detachably affixed to said second end of said elongated spring,
- wherein said first and second spring mounting clamps are positioned a distance from said guided wave sensor on either side of said guided wave sensor,
- wherein an overall height of: 1) said guided wave sensor, 2) said elongated spring, 3) said first spring mounting clamp and 4) second spring mounting clamp is in the range of 0.12 inches to 1.0 inches, and
- wherein said elongated spring and first and second mounting clamps are capable of applying a first pressure to said guided wave sensor at a temperature in the range of 20° C. to 25° C. and applying a second pressure to said guided wave sensor at a temperature in the range of 26° C. to 500° C., wherein said second pressure is in the range of 50% to 99% of said first pressure, when said first and second mounting clamps are mounted to said component and first and second mounting clamps do not contact said component.

9. The sensor clamp of claim 8, wherein said first and second spring mounting clamps each include a mounting body; a mounting post extending from said mounting body on which said elongated spring is fastened; and a removable mechanical fastener that mates with said mounting post and retains said elongated spring on said mounting post.

10. The sensor claim of claim 9, wherein said elongated spring includes a first mounting hole at said first end and a second mounting hole at said second end and said first and second mounting holes are positioned on said mounting posts extending from said first and second spring mounting clamps.

11. The sensor clamp of claim 8, wherein said sensor is cylindrical and said first and second spring mounting clamps are cylindrical and a plurality of said elongated springs are detachably affixed to said first and second spring mounting clamps around a circumference defined by said first and second spring mounting clamps.

12. The sensor clamp of claim 8, wherein said guided wave sensor is a magnetostrictive sensor having a thickness in the range of 0.03 inches to 0.13 inches.

13. The sensor clamp of claim 8, wherein said elongated spring is formed from a nickel-chromium alloy heat treated at a temperature in the range of 900° C. to 1200° C. for a period of 5 to 120 minutes and retains its bias at temperatures in the range of 20° C. to 500° C.

14. A method of deploying a guided wave sensor, comprising:
- positioning a guided wave sensor around a surface of a component;
- positioning at least two spring mounting clamps on either side of said guided wave sensor;
- affixing an elongated spring at a first end and at a second end opposing said first end onto said spring mounting clamps and applying a pressure to said guided wave sensor coupling said guided wave sensor to said component, wherein said spring mounting clamps are positioned around a perimeter of said component and said spring mounting clamps do not contact said component, wherein said pressure is at least 10 psi and the overall height of said guided wave sensor, said spring mounting clamps, and said spring is in the range of 0.12 inches to 1.0 inches.

15. The method of claim 14, wherein said spring mounting clamps are positioned around a perimeter of said component and said plurality of elongated springs are mounted around said perimeter of said component.

16. The method of claim 14, further comprising inducing guided waves through said component and detecting reflected guided waves using said guided wave sensor.

17. The method of claim 16, further comprising comparing said reflected guided waves to a baseline and determining whether anomalies have formed in said component using a controller.

* * * * *